United States Patent [19]
Wright

[11] Patent Number: 6,066,479
[45] Date of Patent: May 23, 2000

[54] TREATMENT FOR THE ENHANCEMENT OF BACTERIAL EXOPOLYSACCHARIDE RECOVERY

[75] Inventor: J. Barry Wright, Alberta, Canada

[73] Assignee: Betzdearborn Inc., Trevose, Pa.

[21] Appl. No.: 09/133,538

[22] Filed: Aug. 13, 1998

[51] Int. Cl.[7] .................................................. C12P 19/04
[52] U.S. Cl. ........................... 435/101; 435/72; 435/104; 435/875
[58] Field of Search .............................. 435/72, 101, 875, 435/104

[56] References Cited

FOREIGN PATENT DOCUMENTS 2226249 6/1996 United Kingdom .
2296249 6/1996 United Kingdom .

OTHER PUBLICATIONS

Evans et al., Journal of Antimicrobial Chemotherapy (1990) 25, 585–591.
Cerning et al., J. Diary Sci., (1992) 75: 692–699.
DuBois et al., Analytical Chemistry, vol. 28, No. 3, Mar. 1956, 350–356.
Buckmire et al., Microbios, (1984), 41, 49–63, 1984.
Lawford et al., "Bioreactor Design Considerations in the Production of High–Quality Microbial Exopolysaccharide," *Applied Biochemistry and Biotechnology*, vol., 28/29, 1991, p. 667–83.

*Primary Examiner*—Herbert J. Lilling
*Attorney, Agent, or Firm*—Greenblum & Bernstein, P.L.C.

[57] ABSTRACT

A treatment for enhancing the recovery of exopolysaccharide from bacterial cells is disclosed, which treatment includes adding to a cultivation medium containing said cells an amount, effective for the purpose of an alkylsulfosuccinate surfactant.

5 Claims, No Drawings

TREATMENT FOR THE ENHANCEMENT OF BACTERIAL EXOPOLYSACCHARIDE RECOVERY

FIELD OF THE INVENTION

The present invention relates to compositions and methods for the recovery of bacterial exopolymers for food, personal care, pharmaceutical, petroleum and other industries requiring high quality viscosifiers, bioemulsifiers and biodegradable polymers.

BACKGROUND OF THE INVENTION

There is an ever increasing demand for inexpensive and environmentally acceptable viscosifiers, bioemulsifiers and biodegradable polymers. The biotechnology industry has responded with increasing the availability of a variety of bacterial cell products that may find their way into commercial use. Although many of the bacterial products offer a wide range of attractive improvements over synthetically produced materials, they remain relatively expensive to produce. The expense is generally associated with costs of recovery and purification of the desired product.

Higher yields of biopolymers are the result of a better understanding of biosynthesis and optimization of fermentation conditions. This satisfies one of the important steps in recovering adequate amounts of the polymer for potential industrial applications. Nonetheless, recovery of these polymers remains a difficult and costly step. Recovery of a biopolymer, regardless of the conditions used to produce it, typically involves a precipitation step; the precipitated biopolymer is recovered by centrifugation.

There are two major inefficiencies associated with a typical recovery protocol. The first problem arises if significant numbers of the producing population are killed by the precipitation protocol. The viable biomass must then be reinoculated and allowed to equilibrate to the conditions optimal for the recovery of the biopolymer. These steps require the addition of nutrients and energy that increase the cost of producing the biopolymer. Another major inefficiency is incomplete recovery of the biopolymer of interest. Different bacterial exopolymers are attached to (or associated with) the producing cells with varying degrees of tenacity. Those bacteria that have relatively securely attached exopolymers are less likely to shed them into the medium, thus reducing the amount of exopolymer available for recovery in the precipitation step.

The compositions of the present invention have demonstrated their ability to significantly increase the recovery of exopolymer from a microbial culture. The materials do not apparently affect the amount of exopolymer produced by the bacterial cells, but serve only to increase the efficiency of exopolymer recovery.

SUMMARY OF THE INVENTION

The present invention provides for compositions and methods for enhancing recovery of exopolysaccharide polymers from bacterial cells. The compositions and methods of the present invention neither interfere with the viability of the producing strains of bacteria, nor enhance the production of the exopolymer; the materials increase exopolymer recovery. The method of the present invention comprises adding to the cultivation medium (i.e., a nutrient solution for microorganisms to grow within) an effective amount of an alkyl-sulfosuccinate surfactant in order to induce the desired response. The method also comprises the inclusion of a nonionic block copolymer in conjunction with the alkylsulfosuccinate that further enhances the recovery of the exopolymer while reducing the required amount of sulfosuccinate.

DESCRIPTION OF THE PREFERRED EMBODIMENTS

The present invention relates to compositions and methods for increasing recovery of bacterial exopolymers from aqueous culture through the addition of an effective amount of sulfosuccinate surfactant or a combination of sulfosuccinate and a nonionic ethylene oxide-propylene oxide block copolymer.

The present inventor has discovered that alkylsulfosuccinates of the general structure $RO_2CCH_2CH(SO_3^-M^+)CO_2R^1$, where $R^1=R$ or $R^1=H$, and $M=Na$ or $K$, greatly enhance recovery of exopolymer from aqueous bacterial cultures. In a preferred embodiment of the present invention, $R=C_8$ or $C_9$, with the $C_9$ form being most preferred.

The timing of addition of the treatment of the present invention to the bacterial culture does not appear to result in a significant alteration in effect observed. Furthermore, the treatment of the present invention has not mediated any toxic effect upon the bacterial strains tested. Since the bacterial population is not adversely affected, the same population can be continually used until such time as the fermentation conditions no longer favor exopolymer production by the particular strain of bacteria.

The method employed to compare the amount of recovered exopolymer involved the growth of the bacteria in a chemically defined medium for a length of time appropriate for the production of bacterial exopolysaccharide. The bacterial cells were removed from the medium by centrifugation and washed, with the wash medium being added to the collected supernatant. The cell pellets were reserved for carbohydrate, protein and deoxyribonucleic acid quantitation. The extracellular carbohydrates from the supernatant were dialyzed to remove any small molecular weight (<12,000 daltons) sugars added as nutrients or eliminated as waste products. Exopolymer recovery was compared to other cell components on a per weight basis.

A number of different organisms were used in the studies on exopolymer production, including *Pseudomonas aeruginosa*, an important industrial organism owing to its production of alginate, as well as *Burkholderii pickettii*. Exopolymer production by other organisms was also examined. Table 1 below shows carbohydrate ratios from *B. pickettii* treated with 0, 5,12 and 24 ppm of dinonylsulfosuccinate added during the growth phase of the organisms (24 hours).

TABLE 1

| Treatment | CHO:DNA | EPS:DNA |
| --- | --- | --- |
| Control | 2.8 | 56.3 |
| 5 ppm | 3.7 | 75.7 |
| 12 ppm | 3.5 | 112.2 |
| 24 ppm | 4.7 | 265.1 |

CHO: carbohydrate
EPS: exopolysaccharide

Table 1 demonstrates that the amount of recoverable exopolymer increased as a function of the amount of dinonylsulfosuccinate added during the growth phase of the organisms. The amount recovered in the presence of 24 ppm, or higher is significantly greater than the control. However, the amount of total cell carbohydrate produced did not change significantly.

In order to further determine the effect of the surfactant upon recovery of exopolymer from treated bacterial cells, the recoveries of exopolymer from treated and control cultures when the surfactant was added to the culture following growth were compared. This was accomplished utilizing the same method as described above for treatment of cell populations during their growth cycle, except that the surfactant (or water, in the case of the control) was added to the growth medium at 24 hours and incubated with the cells for an additional 3 hours. Results of this study are found in Table 2.

TABLE 2

| Treatment | CHO:DNA | EPS:DNA |
| --- | --- | --- |
| Control | 5.3 | 1.7 |
| 48 ppm dinonylsulfosuccinate | 4.8 | 4.9 |

The results in Table 2 indicate that there is no significant difference between the total carbohydrate produced by the bacteria when compared on a per cell basis. However, there is a significant difference in the amount of recovered exopolymer. These results are similar to the data shown earlier (Table 1) demonstrating the recovery of total carbohydrate and exopolymer from cells treated with surfactant during the growth phase.

Some block copolymer surfactants of the Pluronic® type are able to increase the efficacy of the sulfosuccinate in enhancing the recovery of exopolymer from bacterial cells. Note that the Pluronic material, alone, does not increase exopolymer recovery. The Pluronic surfactants that have demonstrated the best efficacy have between 10 and 50% polyoxyethylene, with molecular weights in the range of approximately 1800–4000.

The preferred range of mixture of the surfactants is from a 4:1 to 1:10 ratio of sulfosuccinate: block copolymer, with a 1:1 to 1:2 ratio being particularly preferred. The effective dosage of the treatment of the present invention is from 0.1 ppm to 150 ppm of surfactant, the preferred treatment dose being dependent upon the bacterial species involved.

The enhancement of efficacy is further demonstrated by the following example, although other similar materials are expected to be equally effective. In the following table, the recovery of exopolymer is demonstrated in the presence of 10 ppm sulfosuccinate alone, and 10 ppm sulfosuccinate in combination with an additional 10 ppm of the block copolymer. Carbohydrate ratios from *B. pickettii* treated with 10 ppm of dinonylsulfosuccinate or 10 ppm dinonylsulfosuccinate and 10 ppm block copolymer (mixture) added during the growth phase of the organisms (24 hours, n=3) are shown.

TABLE 3

| Treatment | CHO:DNA | EPS:DNA |
| --- | --- | --- |
| Control | 4.9 | 99.2 |
| Sulfosuccinate | 3.5 | 134.3 |
| Mixture | 4.6 | 267.0 |

As shown above, the combination of sulfosuccinate and block copolymer was effective at producing an increase in the amount of exopolymer recovered from the bacterial culture.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

I claim:

1. A method for enhancing recovery of exopolysaccharide from bacterial cells which comprises including alkylsulfosuccinate surfactant in a cultivation medium, during the growth phase of bacterial cells in the cultivation medium.

2. The method as recited in claim 1 wherein said alkylsulfosuccinate surfactant comprises dialkylsulfosuccinate.

3. The method as recited in claim 1 wherein said alkylsulfosuccinate surfactant comprises alkysulfosuccinate of formula:

$$RO_2CCH_2CH(SO_3^-M^+)CO_2R^1$$

where $R=C_8$ or $C_9$, $R^1=R$ or H and $M=Na$ or K.

4. The method as recited in claim 1 wherein from about 0.1–150 ppm of said alkylsulfosuccinate surfactant is included in said cultivation medium.

5. The method as recited in claim 2 wherein said dialkylsulfosuccinate comprises dinonylsulfosuccinate.

* * * * *